United States Patent [19]
Hess

[11] Patent Number: 5,350,679
[45] Date of Patent: Sep. 27, 1994

[54] REPEAT INSULT MICROBIAL TEST METHOD

[75] Inventor: Carol A. Hess, Vassar, Mich.

[73] Assignee: Dow Corning Corporation, Midland, Mich.

[21] Appl. No.: 75,436

[22] Filed: Jun. 14, 1993

[51] Int. Cl.$^5$ .................. C12Q 1/02; C12Q 1/04; C12N 11/04; C12N 11/00

[52] U.S. Cl. .................... 435/32; 435/4; 435/29; 435/299; 435/301; 435/805; 424/407; 424/413; 424/419

[58] Field of Search ............... 435/32, 29, 31, 805, 435/301, 4, 299; 424/407, 413, 419

[56] References Cited

U.S. PATENT DOCUMENTS 4,962,170  10/1990  Chromecek et al. ............... 526/212
5,206,028   4/1993  Li ................................ 424/484
5,234,688   8/1993  Gaffer ............................ 424/401

OTHER PUBLICATIONS

Lennette et al., (Ed.), Manual of Clinical Microbiology, Third Edition, Amer. Soc. Microbiology, Washington, D.C., 1980, pp. 463–474.

Primary Examiner—Michael G. Wityshyn
Assistant Examiner—Jane A. Williams
Attorney, Agent, or Firm—James L. DeCesare

[57] ABSTRACT

A repeat insult microbial test method in which an antimicrobial agent is applied to a porous permeable substrate. The porous permeable substrate is inoculated with microorganisms, and the porous permeable substrate is incubated for a predetermined period of time, at a temperature which is conducive to the flourishment of the microorganisms. The porous permeable substrate is reinoculated and reincubated a predetermined plurality of times and the inoculated porous permeable substrate is incubated for a final period of time between 18–24 hours at the temperature used previously. The porous permeable substrate is then examined, and the growth of microorganisms is determined.

14 Claims, 1 Drawing Sheet

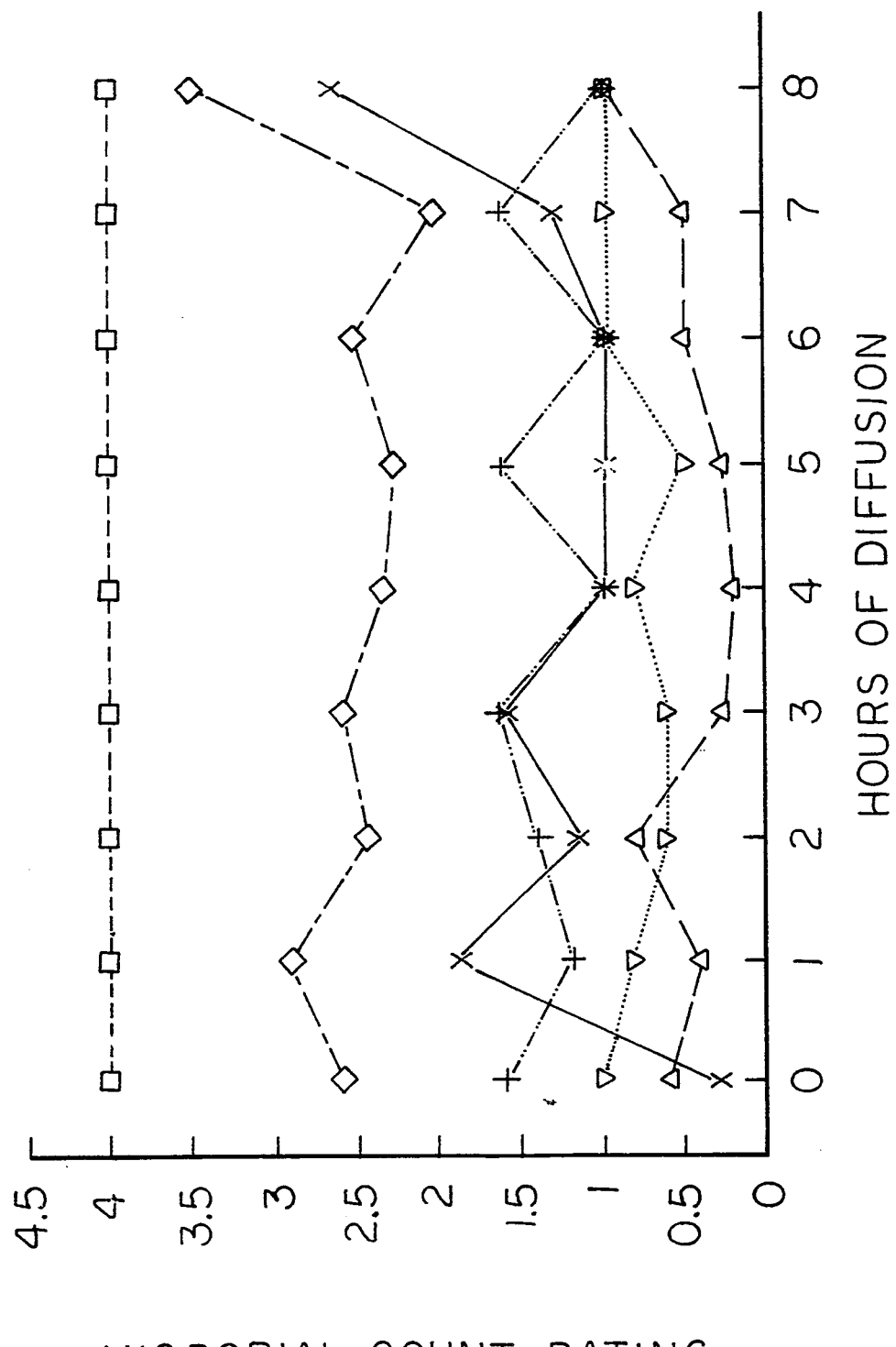

REPEAT INSULT MICROBIAL TEST METHOD

BACKGROUND OF THE INVENTION this invention is directed to a method of determining the effectiveness against microbial growth of certain antimicrobial agents, either alone or as an ingredient of various cosmetic and pharmaceutical products. More particularly, an "in vitro" test method has been devised which is capable of demonstrating the efficacy of an antimicrobial agent in a cosmetic or deodorant product.

The test method of the invention mirrors "in vivo" efficacy and conditions, and provides an indication of how well and for how long an antimicrobial agent is effective in a given product during use. In addition, the test method simulates (i) the dilution effect when the skin is subjected to sweat and microbial attack, and (ii) the diffusion effect of an antimicrobial agent away from the skin as a function of time.

Cosmetic products are particularly vulnerable to contamination by microorganisms, and therefore the control of microbial contamination in cosmetic products is an important aspect of cosmetic manufacturing. Cosmetic products provide a good medium for the growth of various kinds of microorganisms, for such products contain water, oils, gums, protein, polyols, and other nutrients which promote growth.

The presence of viable organisms in cosmetic products can cause separation of emulsions, discoloration, and the formation of unpleasant odors. Decomposition of some of the ingredients of a cosmetic product may lead to skin irritation, and the presence of pathogenic organisms can place the user at the risk of infection.

One safeguard use din the pharmaceutical and cosmetic industry has been to evaluate substances intended for the topical application to human skin, for their propensity to irritate and or sensitize the skin. Traditionally, it has been demonstrated that a product can be safely applied to human skin without significant risk of adverse reaction by "Repeated Insult Patch Testing". This "in vivo" procedure is a predictive patch study that can detect weak sensitizers that require multiple applications in order to induce a cell-mediated immune response sufficient to cause an allergic reaction.

Such "in vivo" procedures are costly and time consuming, and must be administered by qualified and specialized personnel who have been trained in the nuances of the test techniques. Typically, for example, these tests involve the use of a study group of hundreds of volunteer subjects, who are under Federal regulations, required to execute an informed consent document prior to entering the study. The study can extend over about a six week period or more, and involves three phases which are termed an Induction Phase, a Test Phase, and a Challenge Phase.

The Induction Phase involves multiple applications of the topical study product to a test site by means of occlusive and semi-occlusive adhesive patches, and evaluation of the test site prior to reapplication to a site. The Rest Phase can be for two weeks or more. The Challenge Phase involves the application of identical patches to sites previously unexposed to the topical study product. If evidence of sensitization such as erythema is shown by response grading, a Rechallenge Phase is added to the test, in which occlusive and semi-occlusive patches are once more applied to naive test sites, in about 1-2 weeks or more following the Challenge Phase.

Another way that the cosmetic industry evaluates the effectiveness of topical antimicrobial preparations after safety of a substance has been assured is to apply the product to volunteer subjects. This "in vivo" procedure is an actual in-use study that can indicate how well the substance will perform in preventing microbial growth that leads to malodors.

The Induction Phase involves abstinence from particular similar substances to the test substance for a period of about three weeks. The Challenge Phase involves the application of the test substance to sites previously unexposed to the study product and noted for providing an environment conducive to microbial growth. This Challenge Phase of applying the test substance to the area daily can last from three to six weeks. Evaluation of the ability of the test substance to perform can be done by "sniffing" for malodor production of taking actual microbial counts on the test area.

It should be apparent therefore, that a need exists for a simplified and less expensive procedure for testing antimicrobial agents and topical cosmetic an pharmaceutical products containing antimicrobial agents as active ingredients.

The method according to the present invention is believed to meet this need, and is considered unique and distinct from the methods of the prior art, in that it has not heretofore been known to determine microbial characteristics in "repeat insult" testing procedures. Prior "repeat insult" testing has been limited to "in container" preservation applications, and it has not been possible to determine from such "in container" tests, the effectiveness of an antimicrobial agent on the skin. The present method is capable of indicating not only the effectiveness of an antimicrobial agent over time, but in addition, it is capable of demonstrating the efficacy of "entrapped" antimicrobial agents.

SUMMARY OF THE INVENTION

The invention is directed to a repeat insult microbial test method in which an antimicrobial agent is applied to a porous permeable substrate. The porous permeable substrate is inoculated with common skin or environmental microorganisms. The porous permeable substrate is incubated for a predetermined period of time at a temperature which is conducive to the flourishment of the microorganisms. The porous permeable substrate is a re-inoculated and re-incubated a predetermined number of times, but at least twice. The inoculated porous permeable substrate is incubated for a final predetermined period of time between 18-24 hours at the previous temperature. The final incubation is carried out following the final inoculation. The porous permeable substrate is then examined, and the growth of microorganisms on the porous permeable substrate is determined and reported.

These and other features and objects of the herein defined present invention will become more apparent from a consideration of the following detailed description thereof.

BRIEF DESCRIPTION OF THE DRAWINGS

The single figures of drawing is a graphical representation of a typical historical profile of "repeat insult" microbial challenge testing, conducted in accordance with the concept of the present invention.

In the single figure, the effectiveness of free TRICLOSAN in inhibiting growth is depicted as a function of time. The effectiveness of TRICLOSAN delivered in an "entrapped" form is also demonstrated.

DETAILED DESCRIPTION OF THE INVENTION

The method according to the present invention is effective to show the efficacy on human skin of any of the common antimicrobial agents known in the art, including antimicrobial agents containing a silicon atom.

An antimicrobial for purposes of the present invention, is an agent that destroys or inhibits the growth of microorganisms. The major classes of microorganisms are bacteria, fungi including mold and mildew, yeasts, and algae. Microorganisms can be found in the air, waters, the human body, soil, wastes, and on all surfaces. The organisms are deposited from the air, food and drink spills, dust, dirt and tracked in soil, and from human excreta such as sweat, urine, and feces. Organisms grow and multiply when there is available a nutrient source of food such as dirt, organic or inorganic material, and living tissue. For growth and multiplication, organisms require warm temperatures, and moisture. When these conditions exist, microorganisms thrive and flourish.

Microbial growth, as previously noted, leads to many problems such as unpleasant odors ranging from stale to musty and mildew-like, to putrid and foul smelling, and sometimes resembling ammonia. The growths produce unsightly stains, discoloration, and deterioration of many surfaces and materials in which they come into contact. A more serious disadvantage of microbial growth is the production of pathogenic microorganisms, germs, their metabolic products and their somatic and reproductive cell parts, which contribute to the spread of disease, infection, and numerous disorders.

Antimicrobial agents are chemical compositions that are used to prevent such microbiological contaminations by inhibiting, killing and/or removing them and neutralizing their effects of deterioration, defacement, odor, and disease.

Of the diverse categories of antimicrobial agents, quaternary ammonium functional silane compounds represent one class of materials which are applicable for purposes of the present invention.

The organosilicon quaternary ammonium functional silane in accordance with the present invention, is a compound having a formula selected form the group consisting of:

$$Y_{3-a}SiR''N^+R'''R''''R^vX^- \atop R'_a \qquad (I)$$

$$Y_{3-a}SiR''P^+R'''R''''R^vX^- \atop R'_a \qquad (II)$$

$$Y_{3-a}SiR''S^+R'''R^vX^- \atop R'_a \qquad (III)$$

and $$Y_{3-a}SiR''ZX^- \atop R'_a \qquad (IV)$$

wherein in each formula (I)–(IV):
Y is R or RO where R is an alkyl radical of one to four carbon atoms or hydrogen;
a has a value of zero; one or two;
R' is a methyl or ethyl radical;
R" is an alkylene group of one to four carbon atoms;
R''', R'''' and $R^v$ are each independently selected from the group consisting of alkyl radicals of one to eighteen carbon atoms, —CH$_2$C$_6$H$_5$, —CH$_2$CH$_2$OH, —CH$_2$OH, and —(CH$_2$)$_x$NHC(O)R$^{vi}$ wherein x has a value of from two to ten and $R^{vi}$ is a perfluoroalkyl radical having from one to twelve carbon atoms;
X is chloride, bromide, fluoride, iodide, acetate or tosylate; and
Z is a positively charged aromatic pyridinium ring of the formula C$_5$H$_6$N$^+$—.

R in the above formulas are alkyl groups of one to four carbon atoms. Thus, useful as R in this invention are methyl, ethyl, propyl, and butyl radicals. Y can also be RO in which R is an alkyl group as noted, or hydrogen indicating the silanol form, i.e. The hydrolyzate. The value of a is zero, one or two, and R' is a methyl or ethyl radical. Because of the presence of these alkyl radicals, these materials must be stabilized with a solvent. Thus, methoxy groups require methanol and ethoxy groups require ethanol.

R" for purposes of the present invention is an alkylene group of one to four carbon atoms. Thus, R" can be alkylene groups such as methylene, ethylene, propylene, and butylene. R''', R'''' and $R^v$ are each independently an alkyl radical of one to eighteen carbon atoms, —CH$_2$C$_6$H$_5$, —CH$_2$CH$_2$OH, —CH$_2$OH, or —(CH$_2$)$_x$NHC(O)R$^{vi}$. The integer x has a value of from two to ten, and $R^{vi}$ is a perfluoroalkyl radical having from one to twelve carbon atoms. The substituent X is chloride, bromide, fluoride, iodide, acetate or tosylate. Z is a positively charged aromatic pyridinium ring of the formula C$_5$H$_6$N$^+$—.

Preferred for this invention are the quaternary ammonium functional salines of the formula $$Y_{3-a}SiR''N^+R'''R''''R^vX^- \atop R'_a$$

in which R is methyl or ethyl; a ha a value of zero; R" is propylene; R''' is methyl or ethyl; R'''' and $R^v$ are alkyl groups containing one to eighteen carbon atoms, where at least one such group is larger than eight carbon atoms; and X is either chloride, acetate or tosylate.

Specific quaternary ammonium functional salines within the scope of the present invention are represented by compounds having the following formulas:

(CH$_3$O)$_3$Si(CH$_2$)$_3$N$^+$(CH$_3$)$_2$C$_{18}$H$_{37}$Cl$^-$ (CH$_3$O)$_3$Si(CH$_2$)$_3$N$^+$(CH$_3$)$_2$C$_{18}$H$_{37}$Br$^-$ (CH$_3$O)$_3$Si(CH$_2$)$_3$N$^+$(C$_{10}$H$_{21}$)$_2$CH$_3$Cl$^-$ (CH$_3$O)$_3$Si(CH$_2$)$_3$N$^+$(C$_{10}$H$_{21}$)$_2$CH$_3$Br$^-$ (CH$_3$O)$_3$Si(Ch$_2$)$_3$N$^+$(CH$_3$)$_3$Cl$^-$ (CH$_3$O)$_3$Si(CH$_2$)$_3$P$^+$(C$_6$H$_5$)$_3$Cl$^-$ (CH$_3$O)$_3$Si(CH$_2$)$_3$P$^+$(C$_6$H$_5$)$_3$Br$^-$ (CH$_3$O)$_3$Si(CH$_2$)$_3$P$^+$(CH$_3$)$_3$Cl$^-$ (CH₃O)₃Si(CH₂)₃P⁺(CH₆H₁₃)₃Cl⁻

(CH₃O)₃Si(CH₂)₃N⁺(CH₃)₂C₄H₉Cl⁻

(CH₃O)₃Si(CH₂)₃N⁺(CH₃)₂CH₂C₆H₅Cl⁻

(CH₃O)₃Si(CH₂)₃N⁺(CH₃)₂CH₂CH₂OHCl⁻

(CH₃O)₃Si(CH₂)₃N⁺(C₂H₅)₃Cl⁻

(CH₃)₃Si(CH₂)₃N⁺(Ch₃)₂C₁₂H₂₅Cl⁻

(CH₃)₃Si(CH₂)₃N⁺(C₁₀H₂₁)₂CH₃Cl⁻

(Ch₃)₃Si(CH₂)₃N⁺(CH₃)₂C₁₈H₃₇Cl³¹

(CH₃O)₃Si(CH₂)₃C₅H₆N⁺Cl⁻

(HO)₃Si(CH₂)₃C₅H₆N⁺Cl⁻

(C₂H₅O)₃Si(CH₂)₃N⁺(Ch₃)₂C₁₈H₃₇Cl⁻

(CH₃O)₃Si(CH₂)₃N⁺(CH₃)₂(CH₂)₃NH-C(O)(CF₂)₆CF₃Cl⁻

One particularly preferred species of quaternary ammonium functional silane compound corresponding to formula (I) is 3-(trimethoxysilyl)propyldimethyloctadecyl ammonium chloride, often referred to as "TMS" for the sake of simplicity. "TMS" has the structure:

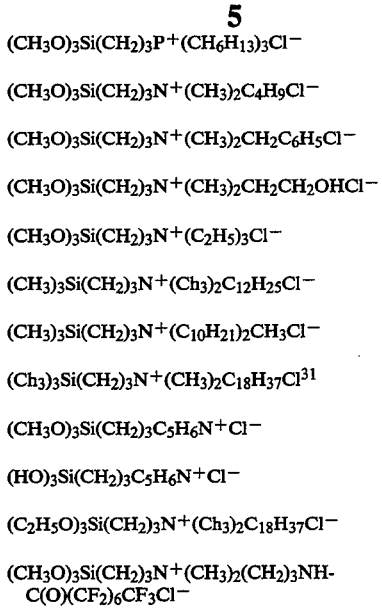

Quaternary ammonium functional salines are compounds which include in the molecular structure, a central nitrogen atom joined to four organic groups, and a negatively charged acid radical such as halogen. The use of a quaternary ammonium functional silane compound is based on the hydrophilic portion of the molecular which bears a positive charge. Since most surfaces are negatively charged, these cationic surface active agents are readily adsorbed to negatively charged surfaces. This affinity for negatively charged surfaces is exhibited by the species 3-(trimethoxysilyl)-propyldimethyloctadecyl ammonium chloride.

In the presence of moisture, this silane imparts a durable, wash resistant, broad spectrum biostatic surface antimicrobial finish to a substrate. This quaternary ammonium functional silane compound is leach resistant, nonmigrating, and is not consumed by microorganisms. It is effective against gram positive and gram negative bacteria, fungi, algae, yeasts, mold, rot, and mildew. This silane is capable of providing durable, bacteriostatic, fungistatic, and algistatic surfaces.

After the silane is applied to a surface, it is chemically bonded to the substrate by condensation of the silanol groups at the surface. What is important is the fact that the durability of any effect produced by the silane as part of a product, requires that the silane molecule react with a surface to a certain extent. The most reactive species, as far as the salines are concerned, is ≡SiOH that is formed by hydrolysis of the alkoxy groups present on the silane. The ≡SiOH groups react with the surface and bind the silane to the surface. It is believed that even though the prime mode of coupling to a surface system is by the route described above, that the alkoxy groups on the silicon atom participate in their own right to bind the silane to a surface.

Methods of making quaternary ammonium functional salines are known in the art and involve the reaction of chloroalkyltrimethoxysilanes and tertiary amines. For example, the specific silane "TMS" can be prepared in accordance with the following scheme:

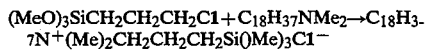

Such bound-type salines function differently from traditional organic unbound agents, in that the bound silane actually attaches itself to the surface to which it is applied, whereas the unbound organic is typically a coating which is not substantive.

This difference is significant, since the silane antimicrobial will continue to prevent reinfestation, and enables one to utilize the intrinsic antimicrobial activity of the silane treated surface to kill transient microbes, long after the unbound organic types of antimicrobials have been depleted of activity. Further, bound salines destroy, reduce, and inhibit the growth and multiplication of bacteria, fungi, and other pathogenic microorganisms, and they accomplish this by the disruption of cell membranes, a mechanism absent from conventional unbound organic antimicrobial materials. Thus, bound silanes provide a prolonged antimicrobial activity, and continue to kill and inhibit the proliferation of potentially destructive microorganisms, versus a mere temporary and superficial protection offered by the unbound category of organic material.

Other suitable antimicrobial agents which can be used for purposes of the present invention, include alcohols such as ethanol or benzyl alcohol; benzoic acid; boric acid; 2-bromo-2-nitropropane-1,3-diol; captan; chloromethyl isothiazolinone; chloroxylenol; dehydroacetic acid; dimethoxane; DMDM hydantoin; formaldehyde; glutaral; isopropyl cresols; MDM hydantoin; parabens; phenoxyethanol; potassium sorbate; potassium undecylenoyl hydrolyzed animal protein; propylene glycol; Quaternium-14; Quaternium-15; resorcinol; sodium benzoate; sodium bisulfite; sodium borate; sodium dehydroacetate; sodium o-phenyl phenate; sodium sulfite; sorbic acid; Triclosan; zinc phenolsulfonate; zinc pyrithione; hexachlorophene; quaternary ammonium compounds such as cetyltrimethyl ammonium bromide, cetyl pryridinium chloride, benzethonium chloride, diisobutyl phenoxy ethoxy ethyl dimethyl benzyl ammoniumchloride, sodium N-lauryl sarcosine, sodium N-polymethyl sarcosine, lauroyl sarcosine, N-myristol glycine, potassium N-lauroyl sarcosine, and stearyl trimethyl ammonium chloride; quaternary ammonium compounds which contain a silicon atom as defined previously; halogenated salicylanilides; chlorhexidine; 6-acetoxy-2,4-dimethyl-m-dioxane; imidazolidinylurea; benzoyl peroxide; urea; salicylic acid; sulphur; glyceryl monolaurate; propyl p-hyroxybenzoate; chlorhexidine gluconate; sodiumlactoyl caprylate; trichlorocarbonilide; zinc undecylenate; sodium bicarbonate; and astringent salts such as sodium aluminum chlorhydroxy lactate.

For the purpose of illustrating the present invention, TRICLOSAN was selected as the antimicrobial agent, since it is a commonly used antimicrobial, either alone or as an ingredient in various personal care consumer products, such as over-the-counter (OTC) or prescription cosmetics and pharmaceuticals. TRICLOSAN is an adopted name assigned by the Cosmetic, Toiletry and fragrance Association (CTFA), of Washington, D.C., for the substituted diphenyl ether compound 5-chloro-2-(2,4-dichlorophenoxy) phenol or $C_{12}H_7Cl_3O_2$. This antimcrobial agent is available commercially as IRGASAN DP-300, a product and tradename of the Ciba-Geigy Corp., of Greensboro, N.C. Any of the other antimicrobial agents enumerated above are equally applicable for purposes of the invention, however.

As previously explained, one unique feature of the method of the present invention, is its ability to demonstrate the efficacy of antimicrobial agents which are "entrapped". This is a significant departure from the prior art, as such techniques are not believed to be known in the art heretofore.

The antimicrobial agent is preferably "entrapped" within particles of a hydrophobic macroporous highly crosslinked polymethacrylate polymer or copolymer.

Macroporous polymethacrylate materials in the form of spherical beads, plugs, and in the form of a complex particulate consisting of unit particles, agglomerates and aggregates, are the subject of numerous US and foreign patents of the Dow Corning Corporation, or Midland, Mich. USA, including US Reissue Patent 33429; U.S. Pat. Nos. 4,855,127; 4,880,617, 4,898,913; 4,848,818; 4,958,999; 4,961,532; 4,962,133; 4,962,170; 5,017,238; 4,035,890; 5,037,485; 5,100,477; 5,102,662; 5,135,660; 5,145,685; 5,173,535; and European Patent 61701.

It is believed to be new and novel in accordance with the present invention, to adapt the test method herein to antimicrobial agents delivered and carried by such polymeric materials, in order to demonstrate the efficay of an "entrapped" antimicrobial agent.

The polymeric material used to entrap the antimicrobial agent in the test method of the present invention is macroporous, due to its complex arrangement of unit particles, agglomerates and aggregates. As a result of this complex structure, the material possesses an inordinate amount of interstitial space, including a vast labyrinth of voids. Volatile ingredients entrapped within the void volume of the material, are released by wicking to the surface, and evaporate at a rate dependent upon temperature, vapor pressure and surface area. Nonvolatile ingredients migrate to the surface by means of capillary action, and can be released on contact with another surface. Mechanical disruption may be used to release an entrapped ingredient.

While the material is shear sensitive, it is not compression sensitive. The material is capable of wicking ingredients from another surface in a sponge-like manner. The material does not shrink or expand, and is capable of adsorbing several times its own weight or an active ingredient. Since the process involved is adsorption in contrast to absorption, the properties of both the polymeric material and the active ingredient are not altered.

Active ingredients are entrapped within the material in contrast to being encapsulated. Encapsulation connotes a complete enclosing of one material within another, such as a shell formed around a core of liquid. Encapsulated ingredients are released by mechanical disruption of the shell or dissolution of the shell, and once the shell is disrupted, the entire contents of the shell are extracted. In entrapment, however, the release of the entrapped ingredient is controlled or sustained by wicking, evaporation and capillary action, and no mechanical disruption is required. Thus, the active ingredient is permitted a relatively unobstructed ingress and egress into and out of the labyrinth of voids of the macroporous polymer.

The discrete particles of the hydrophobic macroporous material of the present invention are capable of entrapping solids and liquids, and are free flowing particulates, even when loaded with an active ingredient. One polymer which is representative of the materials in accordance with the present invention has the formula:

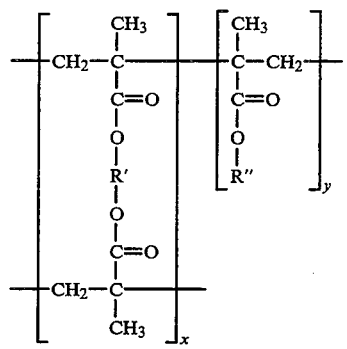

wherein x and y are integers in which the ratio of x:y is from 1:99 to 99:1; R' is an alkylene radical of the formula $(-CH_2CH_2-)_a$ in which a is an integer having a value of from one to eight; and R" is an alkyl group of the formula $-(CH_2)_bCH_3$ in which b has a value of from zero to twenty-nine. Preferably, the ratio of x to y is 80:20, R' is $-CH_2CH_2-$ and R" is $-(CH_2)_{11}CH_3$.

This hydrophobic polymeric material is a highly crosslinked polymetharylate. The material is a product of the Dow Corning Corporation, Midland Mich. USA, and is sold under the trademark POLYTRAP ®. It is a low density, highly porous, free-flowing, white particulate. The particles are capable of adsorbing high levels of lipophilic liquids, while at the same time maintaining a free-flowing particulate character. The polymer can be formed by polymerizing a single polyunsaturated monomer, such as ethylene glycol dimethacrylate or tetraethylene glycol dimethacrylate. Such a process is described in U.S. Pat. No. 4,962,170 which is incorporated herein by reference.

The polymer may also be formed by polymerizing two monomers, at least one of which is a polyunsaturated monomer, with a monounsaturated monomer such as lauryl methacrylate or 2-ethylhexyl methacrylate. Depending upon the process for making the material, the polymer can be produced in the form of (i) a bead having an average diameter of about ten microns to about one hundred-fifty microns; (ii) a plug having a diameter of 45000 microns and a length of 15000 microns; or (iii) a mixed powdered particulate which consists of unit particles, aggregates and agglomerates.

The particulate (iii) is a combined system of particles. The system of particles includes unit particles of less than one micron in average diameter, agglomerates of fused unit particles of twenty to eighty microns in average diameter, and aggregates of clusters of fused agglomerates of two hundred to twelve hundred microns in average diameter. Whether the polymer is in the form of a spherical macroporous bead, a plug, or in the form of the complex macroporous particulate, the structure will entrap various active ingredients.

Precipitation polymerization employing an anhydrous hydrocarbon solvent, is the preferred method for producing the hydrophobic macroporous crosslinked polymer particulate form (iii) of the present invention. In this process, there is polymerized one monounsaturated monomer and one polyunsaturated monomer, in the presence of an excess of a volatile organic liquid which is a solvent for the monomers and the initiator, but not a solvent for the polymer. Polymerization of the monomers is initiated by means of a free radical generating catalytic compound which precipitates a polymer in the solvent in the form of a structure which includes unit particles, aggregates and agglomerates. A dry particulate is formed by removing the volatile hydrocarbon solvent from the precipitated polymeric particulate, leaving behind a structured submicron sized adsorbent material.

Hydrocarbon solvents which may be employed are (i) saturated aliphatic hydrocarbons such as cyclohexane, hexane, and heptane; (ii) aromatic hydrocarbons such as benzene, toluene and xylene; and (iii) aliphatic alcohols such as ethanol, isopropyl alcohol and butyl alcohol. The most preferred solvent is isopropyl alcohol.

The monounsaturated monomer and the polyunsaturated monomer can be present in varying mole ratios such as 20:80, 30:70, 40:60 or 50:50. The process includes the step of stirring the monomers, the solvent, and the free radical generating catalytic compound during polymerization. The particulate is dried by filtering excess solvent from the particulate, and vacuum drying. The empty particulate may be used in its dry empty form in some end use applications, or it can be specially formulated by "post adsorbing" the empty particulate with various functional active ingredients.

Adsorption of active ingredients into the polymeric matrix is achieved by using a stainless steel mixing bowl and a spoon. The active ingredient is simply added to the empty dry particulate in the bowl, and the spoon is used to gently fold the active ingredient into the particulate. Low viscosity fluids may be adsorbed by addition of the fluids to a sealable vessel containing the particulate, and tumbling the materials until the desired consistency is achieved. More elaborate blending equipment such as ribbon or twin cone blenders can also be employed.

The following example illustrates the method of making an adsorbent particulate by precipitation polymerization in an anhydrous hydrocarbon solvent.

EXAMPLE I

Into a five hundred milliliter reactor equipped with a paddle type stirrer, was added and mixed 13.63 grams of ethylene glycol dimethacrylate monomer (eighty mole percent), and 4.37 grams of lauryl methacrylate monomer (twenty mole percent). To the reactor was added 282 grams of isopropyl alcohol as the hydrocarbon solvent, and 0.36 grams of benzoyl peroxide as the catalytic initiator. The monomers and the initiator were soluble in the hydrocarbon solvent, but not the polymer which precipitated. The mixture including the monomers, the hydrocarbon solvent, and the catalytic initiator, was purged with nitrogen. The system was heated in a water bath to sixty degrees Centigrade until polymerization was initiated, and the temperature was increased to 75 degrees for six hours to complete polymerization. During this interval, the polymer precipitated from the anhydrous hydrocarbon solution. The polymerization produced unit particles of a diameter less than one micron. Some of the unit particles adhered and fused together, forming agglomerates of twenty to eighty microns in diameter. Some agglomerates adhered and fused together, forming aggregates of loosely held assemblies of agglomerates of two hundred to twelve hundred microns in diameter. The mixture was filtered to remove excess solvent, and a wet particulate cake was tray dried in a vacuum oven. A dry hydrophobic polymeric particulate consisting of unit particles, agglomerates and aggregates was isolated.

The method of Example I is representative of the precipitation polymerization technique using a hydrocarbon solvent, and in accordance with this technique, the monomers and the initiator are dissolved in a compatible anhydrous hydrocabon solvent in which the monomers and initiator solubilize. The hydrocarbon is a nonsolvent for the polymer, and the polymer in the form of a particulate is precipitated. In contrast to emulsion and suspension polymerization, no surfactant or dispersing aid is required to stabilize the particles. The materials produced are randomly shaped particles, in contrast to suspension polymerized spherically shaped beads. The randomly shaped particulates include unit particles, agglomerates, and aggregates. The volatile hydrocarbon solvent is removed leaving an empty dry particulate. The empty dry particulate is suitable for use in an active-free condition for some end use applications, or it may be "post adsorbed" with a variety of functional active ingredients for other applications.

The particulate of Example I is unique in its ability to absorb liquids, and yet it will remain free flowing. The material provides a regulated release of ingredients which are entrapped therein, and has the capability of functioning as a carrier. The particulates disappear when rubbed upon a surface. This phenomenon is due to the fact that the large aggregates scatter light and provide the appearance of a white particulate, but when rubbed, these shear sensitive large aggregates are decreased in size, approaching the range of visible light, and seem to disappear. The materials, whether loaded or unloaded, possess utility in diverse areas such as cosmetics, toiletries, household, industrial applications, agriculture, and in the pharmaceutical field.

The following example illustrates a bulk polymerization process, in which an organic ester is entrapped "in situ" in the polymer. The system is anhydrous, and no hydrocarbon solvent is employed. The ester remains entrapped in accordance with this example. This method is used to produce large plugs as shown in Example 10 of U.S. Pat. No. 4,855,127, and the plug form has utility in the manufacture of solid tubes and rods, as well as various shaped molded products.

EXAMPLE II

Seven grams of 2-ethylhexyl oxystearate ester was mixed with 1.5 grams of ethylene glycol dimethacrylate, and 1.5 grams of lauryl methacrylate, in a glass test tube. The solution was deaerated for five minutes, and 0.1 milliliters of t-butyl peroctoate was added and mixed while heating to eighty degrees Centigrade in an oil bath. After twenty minutes, the contents of the glass test tube solidified, and the mixture was maintained at the same temperature for an additional hour to assure full polymerization. A heterogeneous white bulk polymer resulted containing the entrapped ester.

The product of Example I differs from the product of Example II, in that a volatile hydrocarbon solvent is used in Example I, and the solvent is removed, which results in a dry empty particulate material which is free of active ingredients. In Example II, a non-volatile functional material is bulk polymerized "in situ", and the active ingredient remains entrapped in the product. In addition, the form of the product in Example II is in a bulk form, or plug, and fills the container, whereas in Example I, the product is particulate.

In contrast to both Examples I and II, suspension polymerization is an alternate technique, and this process is carried out in water. The monomers, active ingredient, and the catalyst, are combined and form beads or droplets in water, and polymerization occurs within each bead. A surfactant or stabilizer such as polyvinyl pyrrolidone is required, to prevent individually formed beads and droplets from coalescing. The resulting beads, with the active material entrapped, have a substantially spherical outer crust or shell, and an interior macroporous structure. The bead is about ten to one hundred-fifty microns in average diameter, depending upon the rate of agitation employed during the process.

Example III illustrates a process for the production of spherical beads by suspension polymerization, and in which an organic ester is entrapped "in situ" within the beads.

EXAMPLE III

Into a two liter three necked flask equipped with a stirrer, thermometer, and a nitrogen purge, 1.2 grams of polyvinyl pyrrolidone was dissolved in 1500 milliliters of water. A solution of 335 grams of 2-ethylhexyl oxystearate ester, 132 grams of ethylene glycoldimethacrylate, thirty-three grams of 2-ethylhexyl methacrylate, and five milliliters of t-butyl peroctoate, was bubbled with nitrogen for five minutes. This mixture was slowly added to the stirred aqueous solution of polyvinyl pyrrolidone at twenty-two degrees Centigrade under nitrogen purge. The temperature was raised to eighty degrees with constant agitation, and maintained for fifteen minutes until polymerization initiated. The temperature was maintained at eighty degrees for an additional two hours to complete the reaction. White beads were collected by filtering away supernatant liquid, and the beads were dried to remove any excess water. The beads had an average diameter of 0.25 to 0.5 millimeters. Other stabilizers and protective colloids such as starch, polyvinyl alcohol, carboxymethyl cellulose, methyl cellulose, or inorganic divalent alkali metal hydroxides such as MgOH, may be used in place of polyvinyl pyrrolidone in this process.

In Example III, macroporous submicron sized particles are produced, and polymerization is conducted in the presence of an active ingredient which does not dissolve or swell the resulting polymer. The monomers and the active ingredient are selected so as to mutually soluble, but insoluble in the aqueous suspending medium. Droplets are formed, and polymerization occurs within the suspended droplets, resulting in the formation of beads or spheres. The active ingredient is polymerized "in situ", and is entrapped and contained within the beads, but the active ingredient is capable of being released. A volatile hydrocarbon solvent or porogenic agent can be substituted for the nonvolatile active ingredient and removed, leaving an empty porous polymer bead product free of "in situ" entrapped active materials. The empty product has utility as such, or it can be "post adsorbed" with an active ingredient and used in that form.

Examples of polyunsaturated monomers which may be employed are ethylene glycol dimethacrylate, triethylene glycol dimethacrylate, tetraethylene glycol dimethacrylate, and propylene, dipropylene and higher propylene glycols; 1,3 butyleneglycol dimethacrylate; 1,4 butanediol dimethacrylate; 1,6 hexanediol dimethacrylate, neopentyl glycol dimethacrylate, bisphenol A dimethacrylate; divinylbenzene and trivinylbenzeen; divinyltoluene and trivinyltoluene; triallyl maleate, triallyl phosphate, diallyl maleate, and diallyl itaconate.

Monounsaturated monomers include methacrylate and acrylates having straight or branched chain alkyl groups with 1 to 30 carbon atoms, preferably 5 to 18 carbon atoms. Preferred monomers are lauryl methacrylate, 2-ethylhexyl methacrylate, methyl methacrylate, methylhexyl methacrylate, butyl methacrylate, isodecyl methacrylate, stearyl methacrylate, cyclohexyl methacrylate, diacetone acrylamide, phenoxyethyl methacrylate, styrene, and tetrahydrofurfuryl methacrylate.

Highly crosslinked polymeric systems consisting of particles of submicron size can be prepared from single monomers having at least two polymerizable unsaturated bonds, and containing no comonomers having a monounsaturated moiety, and such a process is taught in U.S. Pat. No. 4,962,170.

It has been found that entrapped ingredients can be removed mechanically by utilizing an unexpected property of the polymer adsorbent of this invention. The polymer material, while being shear sensitive, it surprisingly not compressive sensitive. Thus, it is possible to apply compressive forces generated by a pair of stainless steel surfaces to the laden adsorbent polymer material, to squeeze out and remove an entrapped active ingredient. The compressive forces do not cause a degenerative effect upon the resulting adsorbent material. During laboratory assimilations of compressive forces utilizing two stainless steel disks and a vice, the polymer adsorbent has been sifted to break up any compacted masses, followed by squeezing out of the entrapped active ingredient.

Similar products for entrapment are sold by Advanced Polymer Systems, Inc. of Redwood City, Calif., under their trademark MICROSPONGE ®, and these products described in numerous of their patents, including U.S. Pat. Nos. 4,690,825; 4,806,360; 4,855,144; 4,873,091; 50284325; 5,073,365; 5,135,740; 5,145,675; 5,156,843; and 5,188,844.

The antimicrobial agent may be "entrapped", for purposes of the method of the present invention, in either POLYTRAP ® or MICROSPONGE ® types of material. Most preferred, are those materials prepared form the monomer pair of styrene and divinylbenzene, or the monomer pair of methyl methacrylate and ethylene glycol dimethacrylate.

The test method of the invention requires the use of a skin or environmental contaminant, which contaminant can be any one or more of the common microorganisms. For example, one or more of the microorganisms *Staphylococcus aureus, Staphylococcus epidermis,* or *E. coli,* can be employed.

A porous permeable substrate is also required, and there can be employed substrates such as collagen film; filter paper; artificial skin; and where not prohibited by law, full thickness human cadaver skin, preferably mounted in suitable glass diffusion cells with the stratum corneum uppermost. For purposes of the present invention, collagen film is the most preferred substrate.

Growth on a substrate is reflected as the quantity of growth observed visually, in accordance with a microbial count expressed in terms of a scale ranging from zero to four in the scale, zero represents no growth; one represents up to one fourth of the substrate as being covered with growth; two represents up to one half of the substrate as being covered with growth; three represents up to three fourths of the substrate as being covered with growth; and four represents in excess of three fourths of the substrate as being covered with growth. An "effective" treatment for purposes of the invention, is considered to be an observed rating of less than about 1.5 microbial count.

The method of the present invention is carried out by applying from 0.005 to about 0.02 grams of an antimicrobial agent to a porous permeable substrate; inoculating the porous permeable substrate with common skin or environmental microorganisms of the type typically found on residential or industrial surfaces, as well as on human skin surfaces including the feet and underarm areas of the body; incubating the inoculated porous permeable substrate for a predetermined period of time ranging from five minutes to about four hours, at a temperature which is conducive to the flourishment of the microorganisms, which is typically a temperature of $35°$ or $-5°$ Centigrade, but which can be as low as room temperature of $20°-25°$ Centigrade; repeating the inoculating and incubating steps a predetermined number of times, but at least twice, and more preferably about two to ten times; incubating the inoculated porous permeable substrate for a final predetermined period of time between 18-24 hours, at the previous temperature; the final incubation being carried out in sequence and following the final inoculation; and then examining and determining the growth of microorganisms on the porous permeable substrate.

This test method is further illustrated by reference to the following example.

EXAMPLE IV

Collagen film was prepared in advance by cutting the film to form several discs, each disc having a diameter of about eighteen (18) millimeters. Mueller-Hinton agar was prepared according to the instructions of the manufacturer, and the agar was sterilized. After cooling in a water bath at forty-five degrees Centigrade, agar petri plates were poured to a thickness of about four (4) millimeters using twenty-five (25) milliliters of agar. The plates were allowed to harden and maintained at room temperature for 24 hours, to allow for the evaporation of excess moisture. The collagen discs were prepared by wiping across each disc, a sample containing an antimicrobial agent. Each disc was wiped until a thin film of the antimicrobial sample adhered to the disc. The amount of antimicrobial sample employed per disc was about 0.01 grams. Each treated disc was placed on a separate agar petri plate using forceps. The forceps were cleaned between each application of an antimicrobial sample, and flamed to remove any residue frog the previously applied antimicrobial sample. A bacterial inoculum was prepared from a fresh culture of common skin and environmental contaminants, which included one or more of the microorganisms *Staphylococcus aureus, Staphylococcus epidermis,* and *E. coli,* by suspending a loopful of the culture in phosphate buffer. A 0.001 milliliter inoculating loop was employed, and a culture of 18-24 hours growth was used in the preparation of the inoculum. The turbidity of the buffer was adjusted to match the 0.5 McFarland Standard. Plates containing the collagen discs were labelled as "0 time"; "1 hour"; "2 hours"; "3 hours"; and up to "8 hours". A separate series of labelled plates were prepared for each antimicrobial sample which was to be tested. At "0 time", 0.001 milliliters of the inoculum was streaked across each treated disc wit the inoculating loop, and the loop was flamed between each transfer of the microorganisms to a particular collagen discs. All of the plates were incubated at $37°$ Centigrade for one hour. Following incubation, all plates labelled "1 hour" were re-inoculated according to the procedure used at "0 time". These plates were incubated at $37°$ Centigrade for one hour. Between inoculations, the inoculum was maintained in a refrigerator. Following the second incubation, all plates labelled "2 hours" were re-inoculated according to the procedure used at "1 hour". These plates were incubated at $37°$ Centigrade for one hour. This procedure was repeated until all of the plates labelled "0 time" to "8 hours" had been inoculated and incubated. Following the final inoculation, all of the plates were incubated for 18-24 hours. The plates were examined for growth by visual observation, and each of the plates was graded in accordance with a microbial count expressed in terms of a scale ranging from zero to four. In the scale employed, zero represented no growth; one represented up to one fourth of the substrate as being covered with growth; two represented up to one half of the substrate as being covered with growth; three represented up to three fourths oft he substrate as being covered with growth; and four represented in excess of three fourths of the substrate as being covered with growth. As noted above, an "effective" treatment for purposes of the invention was considered to be an observed rating of less than about 1.5 microbial count. The antimicrobial sample used in Example IV was TRICLOSAN. The single figure of the drawing shows a graphical representation of the results of the method carried out in accordance with the procedures described in Example IV.

In the single FIGURE of the drawing, the square labelled "NO ACTIVE" was used as the control, and constituted a solvent solution without TRICLOSAN. The antimicrobial sample indicated by the "+" was a 0.2 percent by weight solvent solution containing TRICLOSAN. The antimicrobial samples indicated by the triangle and the rotated square were solutions containing 0.6 percent by weight of TRICLOSAN "entrapped" in a hydrophobic macroporous highly crosslinked copolymer. The monomers used to prepare the copolymer indicated by the triangle were styrene and divinylbenzene, while the monomers used to prepare the copolymer indicated by the rotated square were methyl methacrylate and ethylene glycol dimethacrylate. These antimicrobial samples were prepared by dissolving TRICLOSAN in acetone, blending the solution with the copolymer, and evaporating the acetone. The antimicrobial samples indicated by the upside down triangle and the "X" was a solution containing 0.05 percent by weight of free TRICLOSAN, and 0.6 percent by weight of TRICLOSAN "entrapped" in a hydrophobic macroporous highly crosslinked copolymer. The monomers used to prepare the copolymer indicated by the upside triangle were styrene and divinylbenzene, while the monomers used to prepare the copolymer indicated by the "X" were methyl methacrylate and ethylene glycol dimethacrylate. These antimicrobial samples were prepared as described above.

The single figure of the drawing reveals that all but one of the test antimicrobial samples were "effective" according to the invention, in that the samples had a microbial count rating of generally less than about 1.5, as shown in the drawing figure. Of particular significance is the fact that the procedure was shown to possess the capability of demonstrating the efficacy of "entrapped" antimicrobial agents.

Other variations and modifications may be made in the compounds, compositions, and methods, described herein, without departing from the essential features and concepts of the present invention. The forms of the invention described herein are exemplary only, and are not intended as limitations on the scope of the invention, as defined in the appended claims.

That which is claimed is:

1. A method for conducting a repeat insult microbial test comprising the steps of (i) applying an antimicrobial agent to a porous permeable substrate selected from the group consisting of collagen film, filter paper, artificial skin, and full thickness human cadaver skin; the antimicrobial agent being applied to the porous permeable substrate in a form in which the antimicrobial agent is entrapped as an active ingredient in a nontoxic hydrophobic macroporous highly crosslinked polymer; (ii) inoculating the porous permeable substrate with at least one microorganism selected from the group consisting of *Staphylococcus aureus, Staphylococcus epidermis,* and *Escherichia coli;* (iii) incubating the inoculated porous permeable substrate for a first predetermined period of time at a first temperature which is conducive to the growth and multiplication of the microorganism; (iv) repeating the inoculating and incubating steps (ii) and (iii) a predetermined number of times but at least twice; (v) incubating the inoculated porous permeable substrate for a final predetermined period of time in excess of the first predetermined period of time at the first temperature; the final incubation step (v) being carried out following the last inoculation in step (iv); and (vi) examining and determining the amount of growth of microorganisms covering the porous permeable substrate.

2. A method according to claim 1 in which the nontoxic hydrophobic macroporous highly crosslinked polymer is formed from at least one polyunsaturated monomer.

3. A method according to claim 2 in which the polyunsaturated monomer is selected from the group consisting of ethylene glycol dimethacrylate and tetraethylene glycol dimethacrylate.

4. A method according to claim 2 in which the macroporous polymer is formed from at least one monounsaturated monomer and at least one polyunsaturated monomer.

5. A method according to claim 4 in which the monounsaturated monomer is selected form the group consisting of styrene, methyl methacrylate, lauryl methacrylate, and ethylhexyl methacrylate; and the polyunsaturated monomer is selected from the group consisting of divinylbenzene, ethylene glycol dimethacrylate, and tetraethylene glycol dimethacrylate.

6. A method according to claim 1 in which the macroporous polymer is in the form of a particulate material which includes unit particles having an average diameter of less than one micron; agglomerates formed of fused unit particles and having an average diameter of about twenty to eighty microns; and aggregates formed of clusters of fused agglomerates and having an average diameter of two-hundred to twelve-hundred microns.

7. A method according to claim 1 in which the macroporous polymer is in the form of a plurality of spherical beads each having a diameter in the range of 10 to 150 microns.

8. A method for conducting a repeat insult microbial test comprising the steps of (i) applying 0.005 to about 0.02 grams of an antimicrobial agent to a porous permeable substrate selected from the group consisting of collagen film, filter paper, artificial skin, and full thickness human cadaver skin; the antimicrobial agent being applied to the porous permeable substrate in a form in which the antimicrobial agent is entrapped as an active ingredient in a nontoxic hydrophobic macroporous highly crosslinked polymer; (ii) inoculating the porous permeable substrate with at least one microorganism selected from the group consisting of *Staphylococcus aureus, Staphylococcus epidermis,* and *Escherichia coli;* (iii) incubating the inoculated porous permeable substrate for a first predetermined period of time ranging from five minutes to about four hours at a temperature ranging from 20° to 40° Centigrade; (iv) repeating the inoculating and incubating steps (ii) and (iii) a predetermined number of times in the range of two to ten times; (v) incubating the inoculated porous permeable substrate for a final predetermined period of time between 18-24 hours at the temperature used in step (iii); the final incubation step (v) being carried out following the last inoculation in step (iv); and (vi) examining and determining the amount of growth of microorganisms covering the porous permeable substrate.

9. A method according to claim 8 in which the nontoxic hydrophobic macroporous highly crosslinked polymer is formed from at least one polyunsaturated monomer.

10. A method according to claim 9 in which the polyunsaturated monomer is selected from the group consistent of ethylene glycol dimethacrylate and tetraethylene glycol dimethacrylate.

11. A method according to claim 9 in which the macroporous polymer is formed from at least one monounsaturated monomer and at least one polyunsaturated monomer.

12. A method according to claim 11 in which the monounsaturated monomer is selected from the group consisting of styrene, methyl methacrylate, lauryl methacrylate, and 2-ethylhexyl methacrylate; and the polyunsaturated monomer is selected from the group consisting of divinylbenzene, ethylene glycol dimethacrylate, and tetraethylene glycol dimethacrylate.

13. A method according to claim 8 in which the macroporous polymer is in the form of a particulate material which includes unit particles having an average diameter of less than one micron; agglomerates formed of fused unit particles and having an average diameter of about twenty to eighty microns; and aggregates formed of clusters of fused agglomerates and having an average diameter of two-hundred to twelve-hundred microns.

14. A method according to claim 8 in which the macroporous polymer is in the form of a plurality of spherical beads each having a diameter in the range of 10 to 150 microns.

* * * * *